(12) United States Patent
Chayat et al.

(10) Patent No.: US 11,033,194 B2
(45) Date of Patent: Jun. 15, 2021

(54) DETECTING AND MEASURING CORRELATED MOVEMENT WITH MIMO RADAR

(71) Applicant: VAYYAR IMAGING LTD., Yehud (IL)

(72) Inventors: Jonathan Chayat, Kfar Sava (IL); Mariana Sarely, Netania (IL); Eli Aloni, Kohav Yair (IL); Ian Podkamien, Petach Tikva (IL); Noam Sol Yarkoni, Ramat Gan (IL)

(73) Assignee: VAYYAR IMAGING LTD., Yehud (IL)

( * ) Notice: Subject to any disclaimer, the term of this patent is extended or adjusted under 35 U.S.C. 154(b) by 0 days.

(21) Appl. No.: 16/983,004

(22) Filed: Aug. 3, 2020

(65) Prior Publication Data

US 2020/0405164 A1    Dec. 31, 2020

Related U.S. Application Data

(63) Continuation of application No. 16/282,650, filed on Feb. 22, 2019, now Pat. No. 10,729,339.

(Continued)

(51) Int. Cl.
*A61B 5/024* (2006.01)
*A61B 5/08* (2006.01)
(Continued)

(52) U.S. Cl.
CPC ...... *A61B 5/02444* (2013.01); *A61B 5/02405* (2013.01); *A61B 5/0816* (2013.01); *G01S 7/41* (2013.01); *G01S 13/42* (2013.01)

(58) Field of Classification Search
CPC ............ A61B 5/02444; A61B 5/02405; A61B 5/0816; G01S 7/41
See application file for complete search history.

(56) References Cited

U.S. PATENT DOCUMENTS 6,697,660 B1 * 2/2004 Robinson ............. A61B 5/4094
                                                        600/409
8,454,528 B2 * 6/2013 Yuen ..................... G01S 13/583
                                                        600/534

(Continued)

FOREIGN PATENT DOCUMENTS

JP        2006186804 A    7/2006
WO    WO 2017/136610 A2   11/2007
(Continued)

OTHER PUBLICATIONS

International Search Report for PCT Application No. PCT/IB2019/051460 dated May 24, 2019.

(Continued)

*Primary Examiner* — Bernarr E Gregory
*Assistant Examiner* — Nuzhat Pervin
(74) *Attorney, Agent, or Firm* — Mark Cohen; Pearl Cohen; Zedek Latzer Baratz

(57) ABSTRACT

A MIMO radar apparatus using correlated motion decomposed from reflectance data of multiple time frames to enhance discriminatory capacity in imaging. The MIMO radar apparatus includes power saving measures and has application in tracking temporal patterns of respiratory and cardiac activities in addition to recognition of targets within non-stationary environments.

18 Claims, 15 Drawing Sheets

Related U.S. Application Data

(60) Provisional application No. 62/689,260, filed on Jun. 25, 2018, provisional application No. 62/633,676, filed on Feb. 22, 2018.

(51) Int. Cl.
    *G01S 13/42* (2006.01)
    *G01S 7/41* (2006.01)

(56) References Cited

U.S. PATENT DOCUMENTS

| | | | | |
|---|---|---|---|---|
| 8,750,971 | B2* | 6/2014 | Tran | A61B 5/1117 600/509 |
| 9,149,244 | B2* | 10/2015 | Anderson | A61B 6/037 |
| 9,229,102 | B1* | 1/2016 | Wright | G01S 13/887 |
| 9,316,727 | B2* | 4/2016 | Sentelle | G01S 13/42 |
| 9,549,691 | B2* | 1/2017 | Tran | A61B 5/369 |
| 9,671,492 | B2* | 6/2017 | Diewald | B60R 21/01534 |
| 2008/0082018 | A1* | 4/2008 | Sackner | A61B 5/113 600/538 |
| 2010/0130873 | A1* | 5/2010 | Yuen | A61B 5/0022 600/484 |
| 2010/0152600 | A1* | 6/2010 | Droitcour | A61B 5/1114 600/534 |
| 2010/0240999 | A1* | 9/2010 | Droitcour | A61B 5/7203 600/453 |
| 2010/0249630 | A1* | 9/2010 | Droitcour | A61B 5/1113 600/529 |
| 2010/0249633 | A1* | 9/2010 | Droitcour | G01S 13/88 600/534 |
| 2010/0292568 | A1* | 11/2010 | Droitcour | A61B 5/7221 600/425 |
| 2011/0237939 | A1* | 9/2011 | Melamed | G06T 5/50 600/425 |
| 2011/0251493 | A1* | 10/2011 | Poh | G06K 9/624 600/477 |
| 2013/0113647 | A1* | 5/2013 | Sentelle | G01S 13/887 342/22 |
| 2014/0235965 | A1* | 8/2014 | Tran | A61B 5/7267 600/301 |
| 2014/0378815 | A1* | 12/2014 | Huang | G01R 33/4808 600/409 |
| 2015/0301167 | A1* | 10/2015 | Sentelle | G01S 13/888 342/22 |
| 2015/0309166 | A1* | 10/2015 | Sentelle | G01S 13/887 342/22 |
| 2016/0209506 | A1 | 7/2016 | Longstaff et al. | |
| 2016/0361041 | A1* | 12/2016 | Barsimantov | G16H 50/30 |
| 2017/0086672 | A1* | 3/2017 | Tran | A61B 8/08 |
| 2017/0205502 | A1* | 7/2017 | Honma | G01S 13/42 |
| 2017/0287206 | A1* | 10/2017 | Solteszova | A61B 8/466 |

FOREIGN PATENT DOCUMENTS

| | | | | |
|---|---|---|---|---|
| WO | WO-2007136610 | A2 * | 11/2007 | A61B 5/0205 |
| WO | WO 2017/002103 | A1 | 1/2017 | |
| WO | WO-2017002103 | A1 * | 1/2017 | G08B 21/043 |

OTHER PUBLICATIONS

Supplementary European Search Report for European Patent Application No. 19758143.2 dated Mar. 23, 2021.

* cited by examiner

DETECTING AND MEASURING CORRELATED MOVEMENT WITH MIMO RADAR

FIELD

This application relates to detecting, locating, and imaging objects by microwave or millimeter-wave reflection, and, in particular, to the use of multiple input/multiple output (MIMO) radar apparatus to detect and measure correlated movement among and/or within parts of a complex target object or of multiple target objects.

BACKGROUND

Wideband MIMO radar apparatus based on compact antenna arrays is currently used in various imaging applications to visualize near-field as well as far-field objects and characterize them based on their reflective properties.

Current state of the art techniques use MIMO radar signal to create 3D images. However, current MIMO imaging techniques lack the ability to achieve adequate resolvability when identifying targets in close proximity to each other or are found in a moving environment.

Complex target objects having different parts, each having their own mode of movement further complicate imaging with sufficient resolvability. Therefore, there is need to advance current MIMO radar imaging techniques to achieve a higher degree of resolvability.

SUMMARY

There is provided according to the teaching of present invention, a multiple-input/multiple-output radar-based method using correlated movement to identity an object set, the method including: transmitting a plurality of transmitted radar signals towards a target object set, each signal of the plurality of signals emanating from a separate radar antenna; receiving reflected radar signals, each of the reflected radar signals having an amplitude attenuation and a phase shift relative to the transmitted radar signal; and decomposing the reflected radar signals into signal elements, each of the signal elements having a spatial component and a temporal component.

According to a further feature of the present invention, there is also provided computing a periodicity of each of the signal elements from the temporal component associated with each of the signal elements.

According to a further feature of the present invention the periodicity is a breathing rate or a heart rate.

According to a further feature of the present invention, there is also provided computing a variance in the heart rate; and outputting the variance in the heart rate.

According to a further feature of the present invention the decomposing of the reflected radar signals is implemented through Blind Signal Separation. Independent Component Analysis, Principal Component Analysis, or Singular Value Decomposition.

There is also provided according to the teachings of the present invention a multiple-input/multiple-output radar-based method using correlated movement to identity an object set, the method including: transmitting a plurality of transmitted radar signals towards a target object set, each signal of the plurality of signals emanating from a separate radar antenna; receiving reflected radar signals, each of the reflected radar signals having an amplitude attenuation and a phase shift relative to the transmitted signal; assigning a voxel value to each voxel in accordance with a collective amplitude attenuation and a collective phase shift of the reflected radar signals; and decomposing the voxel values into voxel elements, each of the voxel elements having a spatial component and a temporal component.

According to the features of the current invention, there is also provided computing a periodicity of each of the voxel elements from the temporal component associated with each of the voxel elements.

According to the features of the current invention, the periodicity is a breathing rate or a heart rate.

According to the features of the current invention, there is also provided computing a variance in the heart rate; and outputting the variance in the heart rate.

According to the features of the current invention, the decomposing the voxel values is implemented through Blind Signal Separation or Independent Component Analysis.

According to the features of the current invention, the decomposing the voxel values is implemented through Independent Component Analysis.

According to the features of the current invention, the decomposing the voxel values is implemented through Principal Component Analysis.

According to the features of the current invention, the decomposing the voxel values is implemented through Singular Value Decomposition.

There is also provided according to the teachings of the present invention a multiple-input/multiple-output radar-based system for using correlated movement to identity an object set, the system including: a radar antenna array; at least one transmit/receive module configured to transmit radar signals and receive reflected radar signals through the antenna array; a configurable activation module enabling energy saving measures in communication with the transmit/receive module; and a processor coupled to the array, the processor operative to: decompose the reflected radar signals into signal elements, each of the signal elements having a spatial component and a temporal component.

According to the features of the current invention, the activation module is configurable to set frame capture rate.

According to the features of the current invention, the frame capture rate is defined by a threshold number of system cycles.

According to the features of the current invention, the activation module is configurable to set a time slot of frame capture.

According to the features of the current invention, the slot of frame capture is set in accordance with frame capture rate.

According to the features of the current invention, the processor is further configured to compute a periodicity of each of the signal elements from the temporal component associated with each of the signal elements.

According to the features of the current invention, the periodicity is a breathing rate or a heart rate.

According to the features of the current invention, the processor is further configured to compute a variance in the heart rate.

According to the features of the current invention, the unique correlated movement among parts of a complex object is selected from a group consisting of coordinated movement of body limbs, head turning, hand gesture, and changes in body posture.

There is also provided according to the teachings of the present invention A multiple-input/multiple-output radar-based system for using correlated movement to identity an object set, the system including: a radar antenna array; at least one transmit/receive module configured to transmit radar signals and receive reflected radar signals through the antenna array; a configurable activation module enabling energy saving measures impose a power in communication with the transmit/receive module; and a processor coupled to the array, the processor operative to: assigning a voxel value to each voxel in accordance with a collective amplitude attenuation and a collective phase shift of the reflected radar signals, decompose the voxel value into voxel elements, each of the voxel elements having a spatial component and a temporal component.

According to the features of the current invention, the activation module is configurable to set frame capture rate.

According to the features of the current invention, the frame capture rate is defined by a threshold number of system cycles.

According to the features of the current invention, the activation module is configurable to set a time slot of frame capture.

According to the features of the current invention, the slot of frame capture is set in accordance with frame capture rate.

According to the features of the current invention, the processor is further configured to compute a periodicity of each of the voxel elements from the temporal component associated with each of the voxel elements.

According to the features of the current invention, the periodicity is a breathing rate or a heart rate.

According to the features of the current invention, the processor is further configured to compute a variance in the heart rate.

According to the features of the current invention, the unique correlated movement among parts of a complex object is selected from a group consisting of coordinated movement of body limbs, head turning, hand gesture, and changes in body posture.

BRIEF DESCRIPTION OF THE DRAWINGS

The subject matter disclosed may best be understood by reference to the following detailed description when read with the accompanying drawings in which.

Figure 1:
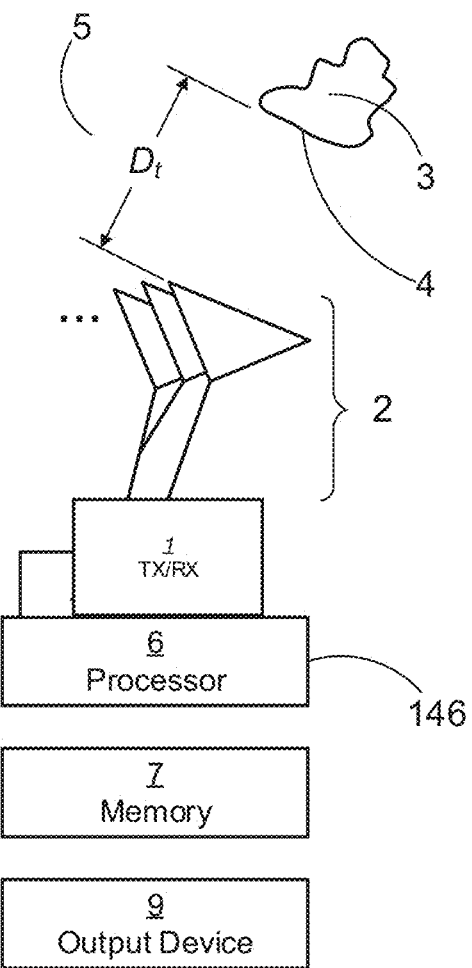
FIG. 1 is a schematic diagram of hardware employed in the MIMO detection system, in accordance with an embodiment of the invention.

It will be appreciated that for simplicity and clarity of illustration, elements shown in the figures are not necessarily drawn to scale and the dimensions of some elements may be exaggerated relative to other elements. In addition, reference numerals may be repeated among the figures to indicate corresponding or analogous elements.

DETAILED DESCRIPTION

In the following detailed description, numerous details are set forth to provide a thorough understanding of the invention. It will be understood by those skilled in the art that the present invention may be practiced without these specific details. In other instances, well-known methods, procedures, and components have not been described in detail so as not to obscure the present invention.

Embodiments of the present invention provide for RF signal processing to detect and obtain measurements from one or more elements of at least one target object. In related embodiments, detection and measurement is furthermore done without having to isolate or identify the specific part or parts which contribute to the correlated movement.

The term "complex target" herein denotes a target object having one or more parts not necessarily distinguished by their respective reflective properties alone (herein denoted as their respective "reflectivities"); but rather, through their correlated movement or motion.

Identification of target objects is based on their elements having dissimilar modes of motion. Similarly, identification of target object from a background is achieved from the contrast of their respective modes of motion.

Some applications provide for further classification of human targets into categories such as "adult", "infant", for example.

Other applications provide identifying regions or parts of the body. The human body is modeled as a collection of rigid bodies (the bones) connected by joints. Rigid bodies have the property that all points on the surface move in a correlated way, since they are all combinations of the 6 degrees of freedom of the rigid body. In these embodiments of the invention the grouping of correlated motions into elements facilitate the identification of regions or parts of the body.

Other applications provide detecting and measuring of physical activities, including but not limited to: walking, running, jumping; coordinated movement of the limbs; carrying objects; head turning; hand gestures; changes in posture; and the like.

Further applications of the present invention provide detecting correlated movement of individuals in specialized environments featuring particular background characteristics and monitoring requirements, including, but not limited to: vehicle interiors and other moving platforms; hospitals and other medical and care facilities; and public venues, non-limiting examples of which include airports and other transportation stations; shopping centers, warehouses, and other commercial establishments; residential and office complexes; museums, theaters, and entertainment halls; parks, playgrounds, and stadiums; and institutions such as schools.

Additional applications of the present invention include: medical and health-related applications; security applications; crowd management applications; and vehicle safety and comfort applications.

According to various embodiments of the present invention, a complex target can include the human body. In these embodiments, the parts of the body include, but are not limited to: the head, the neck, the individual limbs, and the torso. In certain embodiments, physiological activities such as respiration and heartbeat are detectable and measurable, without having to isolate or identify the region of the body responsible for respiration and heartbeat (i.e., the torso).

The term "correlated movement" herein includes movement of one physical element of an object set relative to another, volumetric changes of the elements themselves, changes in orientation, position, shape, contour, or any combination thereof.

The term "measure" and its variants herein denote not only determining quantitative values (including multivariate values), but also analyzing the values, particularly variations in time, and making qualitative characterizations thereof.

The term "voxel element" refers to an entity that has been decomposed from a series of 3D images, each of the images associated with its respective frame.

It should be appreciated that terminology is context dependent. In the context of the physical arena the same terminology is employed when referring to the signal or logical representation of the same entity.

A non-limiting example of such a qualitative characterization involves the measurement of multivariate physiological data, such as the heartbeat and respiration of a subject. Not only can these physiological activities be detected and measured as raw data, but it is also possible to include, as a measurement, a qualitative assessment of the subject's current physical and mental condition based on the breathing rate, heart rate, and heart rate variability. Mental condition is meant to include awareness level, sleepiness, fatigue, anxiety, stress and anger, among other conditions.

Turning now to the figures. FIG. 1 is a schematic block diagram of the MIMO imaging device including an antenna array 2 coupled to a radio frequency (RF) module 1 linked to a processor 6 in communication with memory 7 and output device 9, according to an embodiment. Output device 9 includes visual, audial devices, wireless devices, and printers.

As shown, the reflective elements of face 4 of target object set 3 provide differing reflectance as the radial distance $D_t$ changes with time. Analysis of reflectance data in view of the reflectance data of previous time frames enables detection of correlated movement that advantageously provides discriminatory capability current unavailable in MIMO imaging systems. This is because traditional MIMO imaging systems repetitively construct images based on reflectance data of each time frame; independent of the reflectance data of the previous time frame. Accordingly, the use of correlated motion as differentiation tool constitutes an advance in the art of MIMO imaging.

Figure 2:
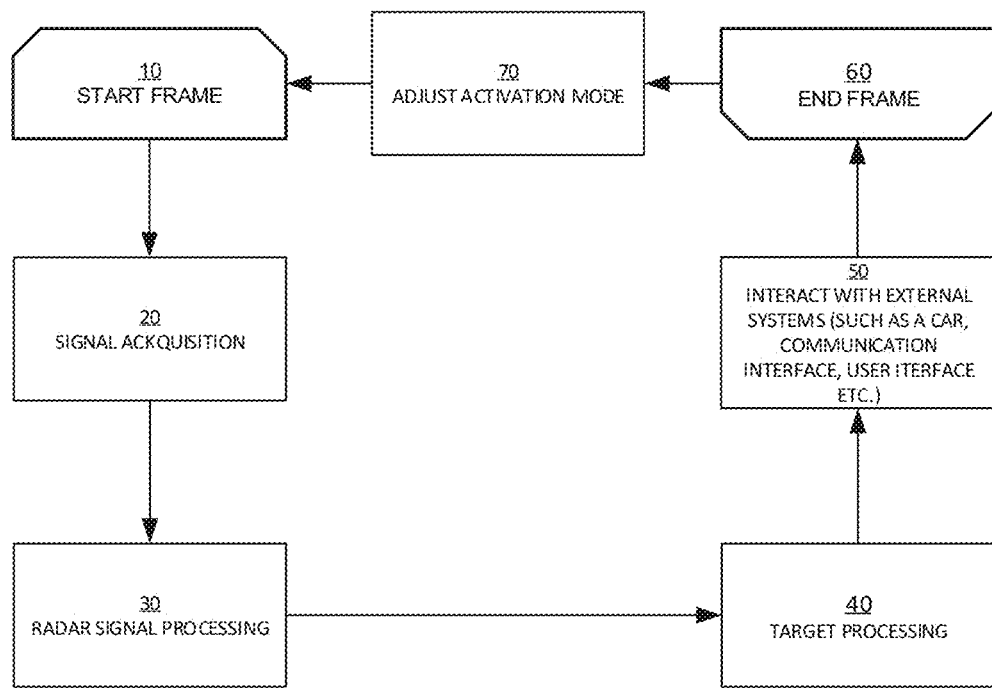
FIG. 2 is an overall flowchart illustrating the processing steps employed, in accordance with an embodiment of the invention.

FIG. 2 is a high-level flowchart illustrating a general processing scheme according to an embodiment of the present invention. The scheme can be described as a closed loop, where each iteration of the loop consists of a sequence of steps.

The loop begins at step 10, where the acquisition and processing of a new time frame is started. Frames are started at regular intervals of $\Delta t$ (meaning the frame rate equals $$\frac{1}{\Delta t}).$$

According to various embodiments of the invention. $\Delta t$ is selected so that target movement $\Delta D$ during $\Delta t$ is small compared to the wavelength of the radar signals $$\left(\text{i.e., } \Delta D \ll \frac{c}{4\pi f}\right)$$

to maintain continuity from one frame to another. For waves having a central frequency f, the wavelength is c/f, where c is the speed of light. When detecting and measuring periodic correlated movement of the target, imaging by a series of frames is a sampling process, so that the frame rate should be set according to the Nyquist criterion to avoid aliasing. Frames are indexed by t=0, 1, 2 . . . corresponding to time, where successive indices represent respective multiples of a $\Delta t$.

In step 20 radar signals are transmitted, received and processed to produce complex phasors, representing the amplitude and the phase of the each received signal relative to each transmitted signals. Step 20 is further elaborated in FIG. 3.

In step 30 several signal processing steps are performed, resulting in a set of components, each consisting of a spatial pattern and a trajectory (displacement vs. time). Step 30 is further elaborated in FIG. 4.

In step 40 components are used to identify targets, classify the targets and estimate target parameters of interest. Step 40 is further elaborated by FIG. 5.

In step 50 the identified targets and their estimated parameters are used to interact with external systems, including, but not limited to, vehicle systems (e.g. to activate a horn, turn on air conditioning, unlock a door etc.), communication interfaces (e.g. to alert a user using his mobile device) or user interfaces (to inform users and allow them to take action).

In step 60 frame processing is ended. In step 70 the system's activation mode is adjusted according to timers, identified targets and their parameters, as well as user inputs. The system activation mode controls parameters including, but not limited to, the number of frames per second the system captures (which determines $\Delta t$) and the transmitting power. In some cases, the system is put in standby mode for a period of time. Activation mode adjustment is done in order to conserve system power. The loop closes when the next frame begins (according to the timing dictated by the activation mode), and the system returns to step 10.

Figure 3:
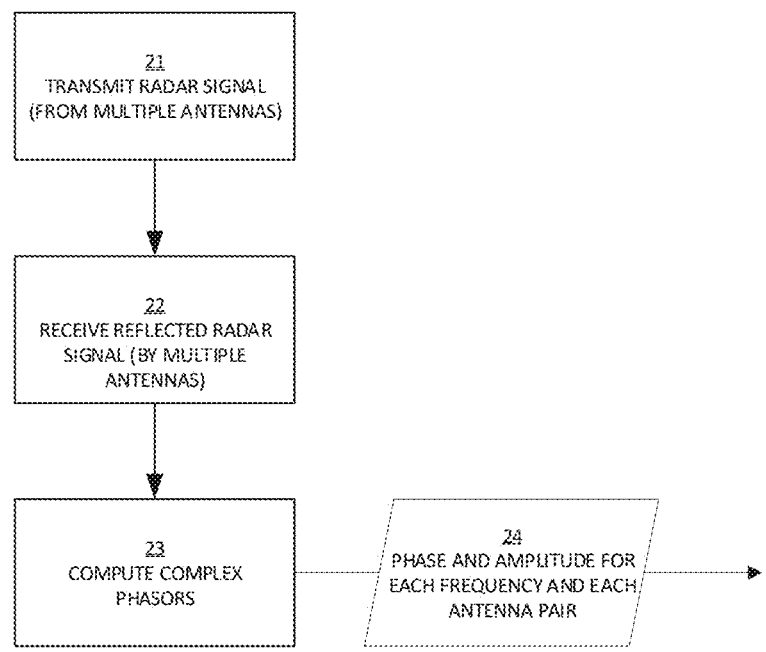
FIG. 3 is an overall flowchart illustrating general processing steps employed, in accordance with an embodiment of the invention.

FIG. 3 is a flowchart elaborating the RADAR SIGNAL ACQUISITION step from FIG. 2 (step 20). In Step 21, radar signals are transmitted from one or more antennas. If multiple antennas are used to transmit, the transmission can be done either sequentially (antenna-by-antenna) or simultaneously. In some embodiments of the invention antennas transmit simultaneously using a coding scheme such as BPSK, QPSK, or other coding schemes as is known in the art. Transmission may include a single frequency, or it may include multiple frequencies.

In step 22 the radar signals which have been reflected by targets in the physical environment surrounding the antennas are received by one or more antennas. Then in step 23 for each transmitted frequency and for each pair of transmitting and receiving antenna the received signals are processed to produce complex phasors, representing the phase and amplitude of the received signal relative to the transmitted signal (item 24).

Figure 4A:
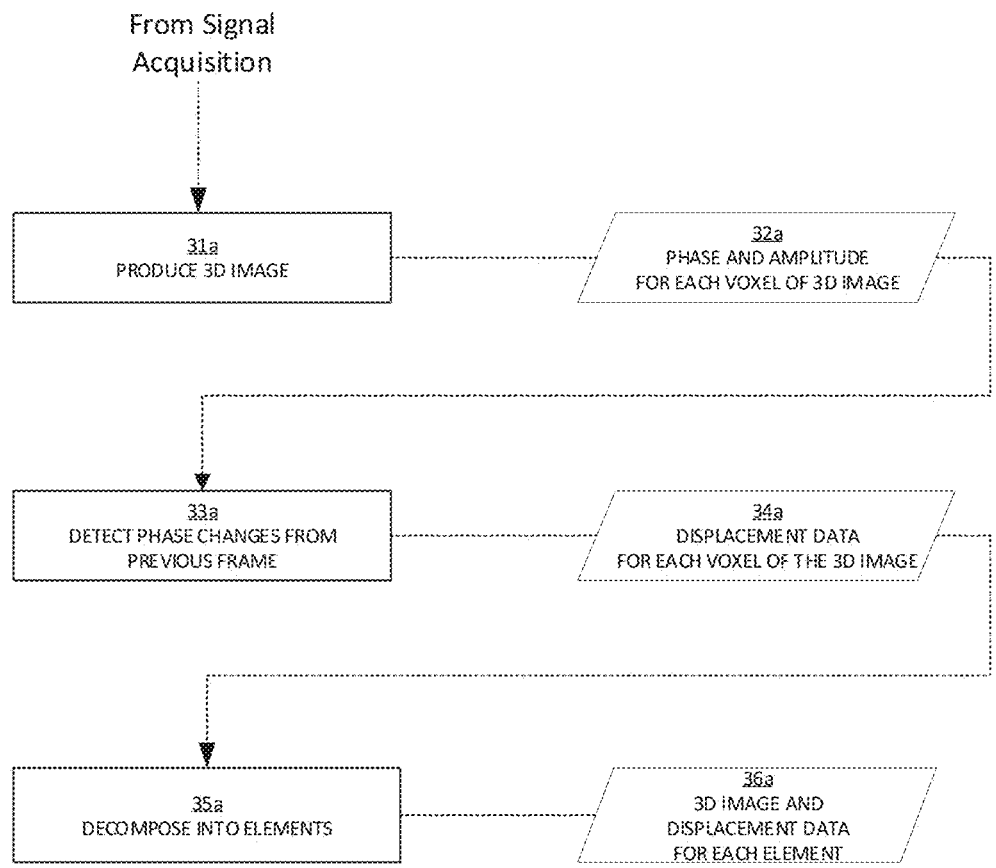
FIG. 4a is a flowchart illustrating the processing steps employed in a first embodiment of the radar signal processing stage, in accordance with an embodiment of the invention.

FIG. 4a is a flowchart elaborating the RADAR SIGNAL PROCESSING step from FIG. 2 (step 30) in an embodiment of the invention. In step 31a a 3D image is produced from the set of complex phasors describing the received signal. The image space representation is conceptually summarized as a data block 32a containing an image matrix $S=[S_{v,t}]$ with a voxel set V whose elements spatially conform to a system of coordinates. The particular system of coordinates for the voxel set can be chosen according to what is most convenient. Common choices include Cartesian coordinates ($v_{x,y,z}$) and polar coordinates ($v_{r,\theta,\varphi}$), but any other coordinate system is equally usable. Each voxel is associated with a single value $S_{v,t}=A_{v,t}e^{j\varphi_{v,t}}$ where $A_{v,t}$ is the amplitude and $\phi_{v,t}$ is the phase associated with a reflector at voxel v. The phase $\phi_{v,t}$ is determined by the radial displacement of the reflector in voxel v from the center of that voxel (designated $D_{v,t}$). The phase is related to the displacement by the following formula:

$$\phi_{v,t} = \frac{4\pi f}{c} D_{v,t}$$

where f refers to the central frequency. A single cycle extends over $2\pi$ radians, but an additional factor of 2 is needed because the reflection doubles the distance the waves travel.

In step 33a the value associated with each voxel at the current frame ($S_{v,t}$) is used together with the value associated with the same voxel at the previous frame ($S_{v,t-1}$), to obtain a robust estimate of the radial displacement between the two frames using the following formula:

$$\widetilde{\Delta D_{v,t}} = \frac{c}{4\pi f} \frac{\mathrm{Im}[S_{v,t} S^*_{v,t-1}]}{|S_{v,t}||S_{v,t-1}| + \lambda \max_v(|S_{v,t}||S_{v,t-1}|) + \epsilon} \quad (1)$$

where $\lambda$ and $\epsilon$ are real scalar parameters that are selected to minimize the effects of noise on the final value. Typical values for $\lambda$ and $\epsilon$ are small, with reasonable values being about 0.1 for $\lambda$ and about $1\times10^{-8}$ for $\epsilon$.

According to another embodiment of the invention a slightly modified version of the formula is used, in order to provide better linearity of the estimated displacement:

$$\widetilde{\Delta D_{v,t}} = \frac{c}{4\pi f} \mathrm{Arg}\left[\frac{S_{v,t} S^*_{v,t-1}}{|S_{v,t}||S_{v,t-1}| + \lambda \max_v(|S_{v,t}||S_{v,t-1}|) + \epsilon}\right] \quad (2)$$

According to an embodiment of the invention, The estimated displacement data ($\widetilde{\Delta D_{v,t}}$) is record (item 34a) using a sliding window (which can be implemented, among other options by using a circular buffer), and in step 35a the radial trajectory component is decomposed into independent elements using Blind Signal Separation (BSS, also known as "Blind Source Separation"). In a related embodiment, the elements of the radial trajectory are separated by using Independent Component Analysis (ICA), a special case of BSS. In another embodiment, the elements of the radial trajectory are separated by Principal Component Analysis (PCA). In another embodiment, the elements of the radial trajectory are separated by Singular Value Decomposition (SVD).

In another embodiment of the invention, an online decomposition algorithm is used, avoiding the usage of a sliding window, allowing the separation of elements to be performed incrementally, frame-by-frame.

$\widetilde{\Delta D_{v,t}}$ is a matrix whose rows represent voxels, and whose columns represent frames. The decomposition algorithm extracts a factorization of $\widetilde{\Delta D_{v,t}}$ in the form of factor triplets ("elements")

$$C_k = (u_{v,k}, \sigma_k, w_{k,t}) \quad (3)$$

where the matrix $[w_{k,t}]$ represents the aggregated frame-dependent (i.e., time-dependent) incremental radial displacements. And the matrix $[u_{v,k}]$ represents a spatial (voxel-dependent) pattern associated with the component.

The incremental radial displacements are summed to obtain an estimated radial displacement trajectory as a function of time:

$$\widetilde{D_{k,t}} = \sum_{t'=t_0}^{t} (w_{k,t'} \sigma_k \max_v u_{v,k}) \quad (4)$$

where the value is normalized to the largest observed incremental movement for the target. The term "summed" herein relates not only to a discrete representation in Equation (4), but also to "integration", according to a related embodiment which calculates the trajectory as an integral.

The spatial pattern $[u_{v,k}]$ and the radial displacement trajectory $\widetilde{D_{k,t}}$ are recorded as item 36a.

Figure 4B:
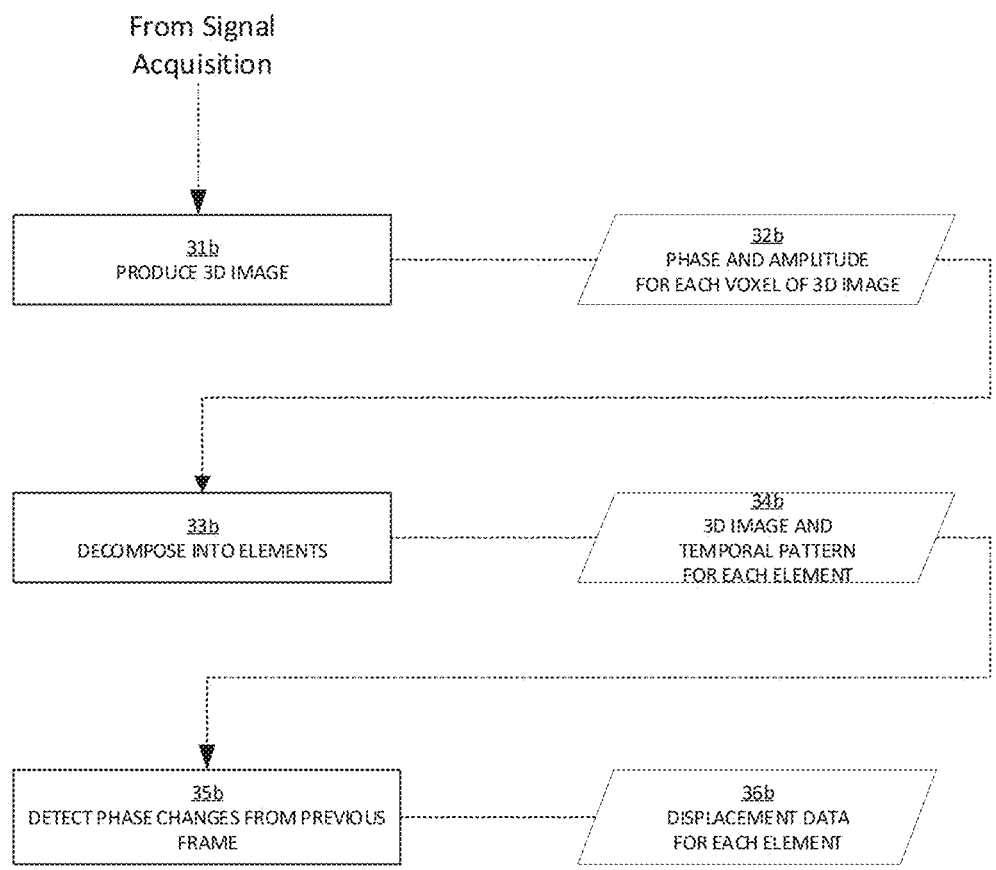
FIG. 4b is a flowchart illustrating the processing steps employed in a second embodiment of the radar signal processing stage, in accordance with an embodiment of the invention.

FIG. 4b is a flowchart elaborating the RADAR SIGNAL PROCESSING step from FIG. 2 (step 30) in an embodiment of the invention (separate from the embodiment described by FIG. 4a). In step 31b a 3D image is produced (item 32b), in a manner similar to the process set forth above in the context of FIG. 4a. In step 33b, the 3D image is decomposed using algorithms similar to those described above; also in the context of FIG. 4a, producing a set of elements, each described by a 3D image and a temporal pattern consisting of complex phasors (item 34b). In step 35b each temporal pattern is processed using a phase detecting procedure similar to the one described above also in the context of FIG. 4a to produce displacement data for each element (item 36b).

Figure 4C:
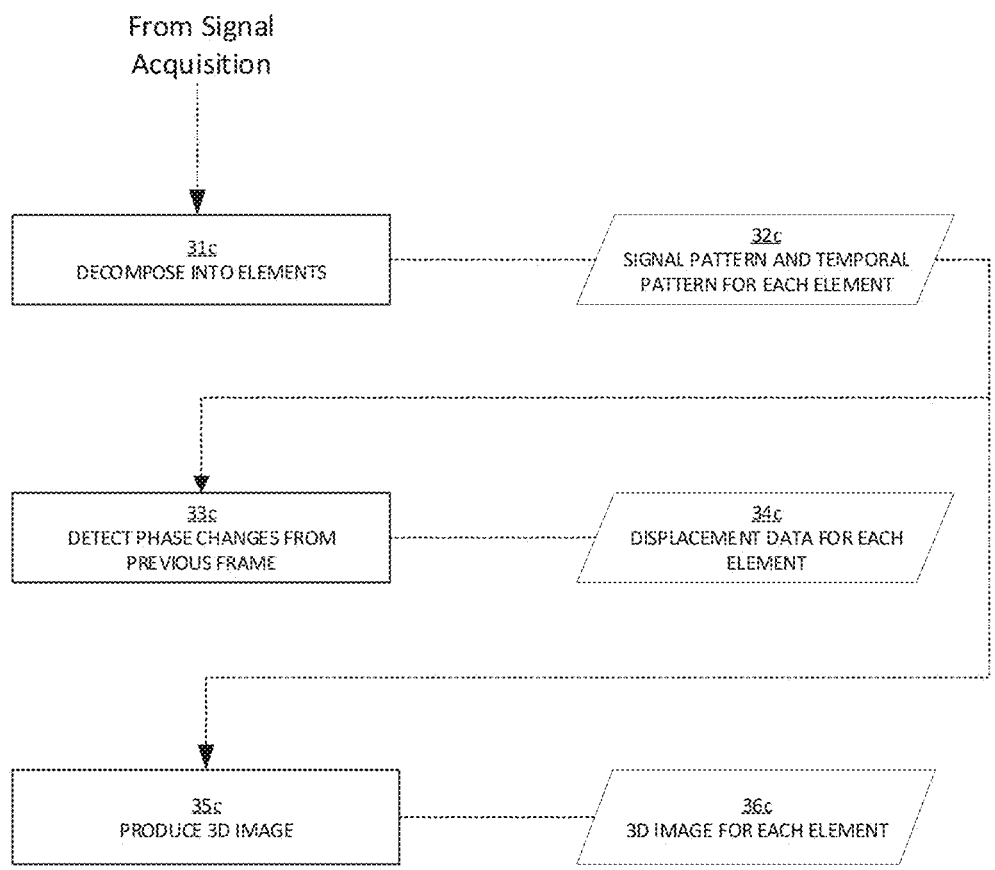
FIG. 4c is a flowchart illustrating the processing steps employed in a third embodiment of the radar signal processing stage, in accordance with an embodiment of the invention.

FIG. 4c is a flowchart elaborating the RADAR SIGNAL PROCESSING step from FIG. 2 (step 30) in an embodiment of the invention (separate from the embodiments described by FIG. 4a and FIG. 4b). In step 31c the complex radar signal is decomposed using algorithms similar to the ones described above also in the context of FIG. 4a, producing a set of elements, each described by a complex time-independent signal pattern and a temporal pattern consisting of complex phasors (item 32c). In step 33c, each temporal pattern is processed using a phase detecting procedure similar to the one described above also in the context of FIG. 4a to produce displacement data for each element (item 34c). In step 35c, each time-independent signal pattern is used to produce a 3D image for the corresponding element (item 36c), in a manner similar to that described above also in the context of FIG. 4a.

Figure 5:
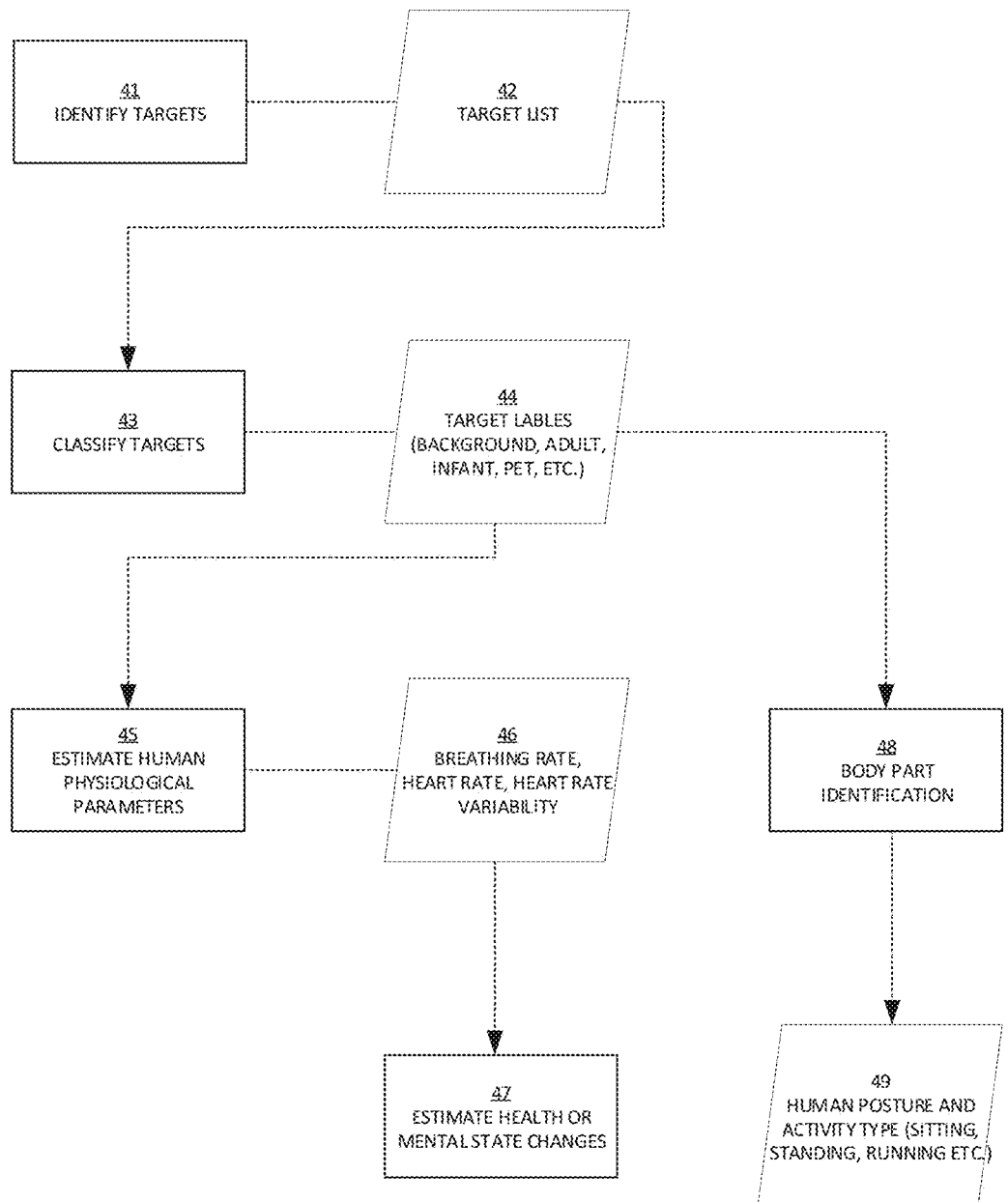
FIG. 5 is a flowchart illustrating the processing steps employed in the target processing stage, in accordance with an embodiment of the invention.

FIG. 5 is a flowchart elaborating the TARGET PROCESSING step from FIG. 2 (step 40) in an embodiment of the invention. In step 41, elements are grouped into targets, representing detected physical objects, by examining the spatial pattern of each element, producing a target list (item 42). In step 43 targets are classified, giving each target a label such as "background" (for example parts of a car interior). "adult", "infant", "pet" etc. (item 44). This classification is done by examining both the spatial pattern and the temporal displacement data for each element within the target.

In step 45, the temporal displacement data of the elements within each human target are used to produce a spectral power distribution model, describing periodicities in the target's movement. In an embodiment of the invention, Welch's method is used to produce the spectral power density model (a non-parametric spectral model). In another embodiment, an (Auto Regressive Moving Average) ARMA model (a parametric spectral model) is used to produce the spectral power density model. Physiological parameters are estimated for human targets, including the breathing rate, heart rate and heart rate variability. Breathing rate and heart rate are estimated from the location of peaks in the spectral power distribution. In an embodiment, using Welch's method, heart rate variability is estimated from the width of the spectral peak corresponding to the heartrate. In another embodiment, using an ARMA model, the heart rate variability is estimated from the parametric representation of the ARMA model itself.

In step 47, the breathing rate, heart rate and heart rate variability are monitored for changes, indicating health or mental state changes.

In step 48, the 3D image associated with each element of a human target is used to identify the element with one or more human body parts. This identification is then used to generate additional data such as human posture and activity type (sitting, standing, running, etc.), as described above.

Figure 6:
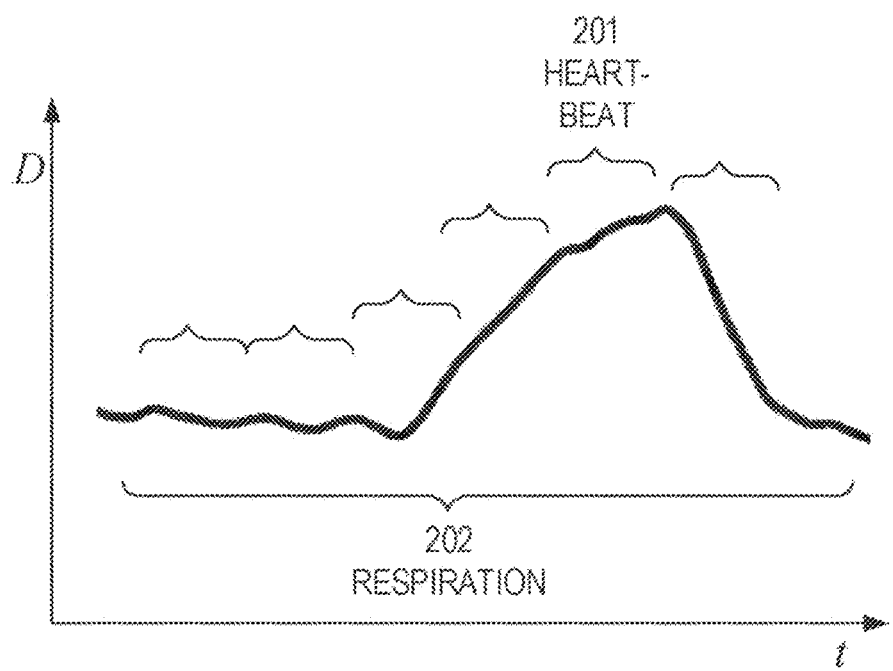
FIG. 6 is a plot of radial displacement as a function of time, as measured for a human subject, in accordance with an embodiment of the invention.

FIG. 6 shows a graph of radial displacement versus time, as measured for a human subject by a method and apparatus according to an embodiment of the present invention. A portion 201 shows a detected heartbeat, and a portion 202 shows a detected respiration. It is noted that according to this embodiment of the invention, it is not necessary to isolate the individual region of the body responsible for heartbeat and respiration.

Figure 7:
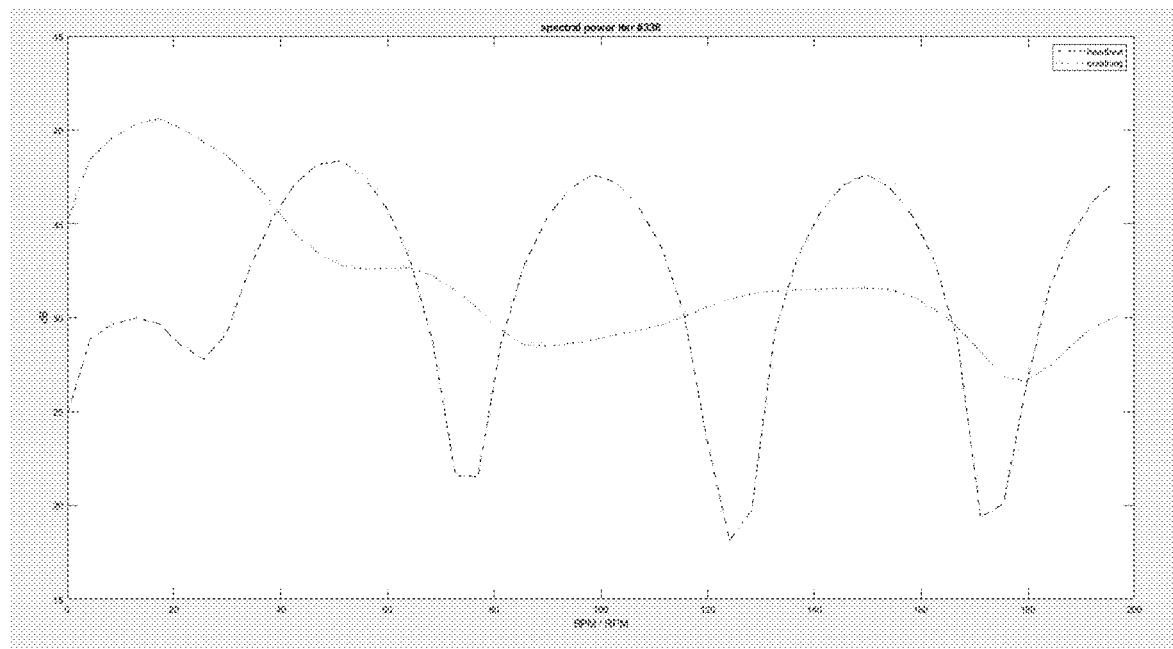
FIG. 7 depicts two plots of spectral power density for two identified elements, in accordance with an embodiment of the invention.

FIG. 7 depicts a plot of the spectral power density of two elements identified by a method and apparatus according to an embodiment of the present invention.

In this embodiment, the sensor has been positioned close to a human subject, the two elements represent two modes of motion, one originating from the respiratory motion of the human subject, and the other originating from the heartbeat motion of the human subject. As can be seen, the elements represent motions which have different periodicity from one another. Each element is then used to calculate the corresponding rate parameter: breathing rate (measured in RPM—respirations per minute), and heart rate (measured in BPM—beats per minute).

FIGS. 8a, 8b, 8c, 8d, and 8e depict image products at various stages of processing of passengers sitting in a car environment.

By way of introduction, a car interior environment has several factors that contribute to the difficulty of identifying and separating passengers from one another and from the car interior background when imaging: passenger proximity, difference in passenger reflectivity, and car vibration.

Passenger proximity refers to passengers sitting next to each other and even contact each other, as is common in the back seat. Accordingly, these backseat passengers can appear as a single target object, when considering reflectance data of each frame separately.

The difference in passenger reflectivity can be very high due to difference in size (e.g. adult vs infant), positioning, and orientation. Differences in passenger reflectivity may degrade detection performance (false positive and false negative rate).

Car vibration also presents a significant challenge for current state of the art MIMO imaging techniques. The difficulty in detecting a change in position is exacerbated as passenger background (the car interior itself) vibrates and alters its reflective properties. As noted above, these imaging obstacles are resolved through the use of correlated motion as the differentiating parameter.

Figure 8A:
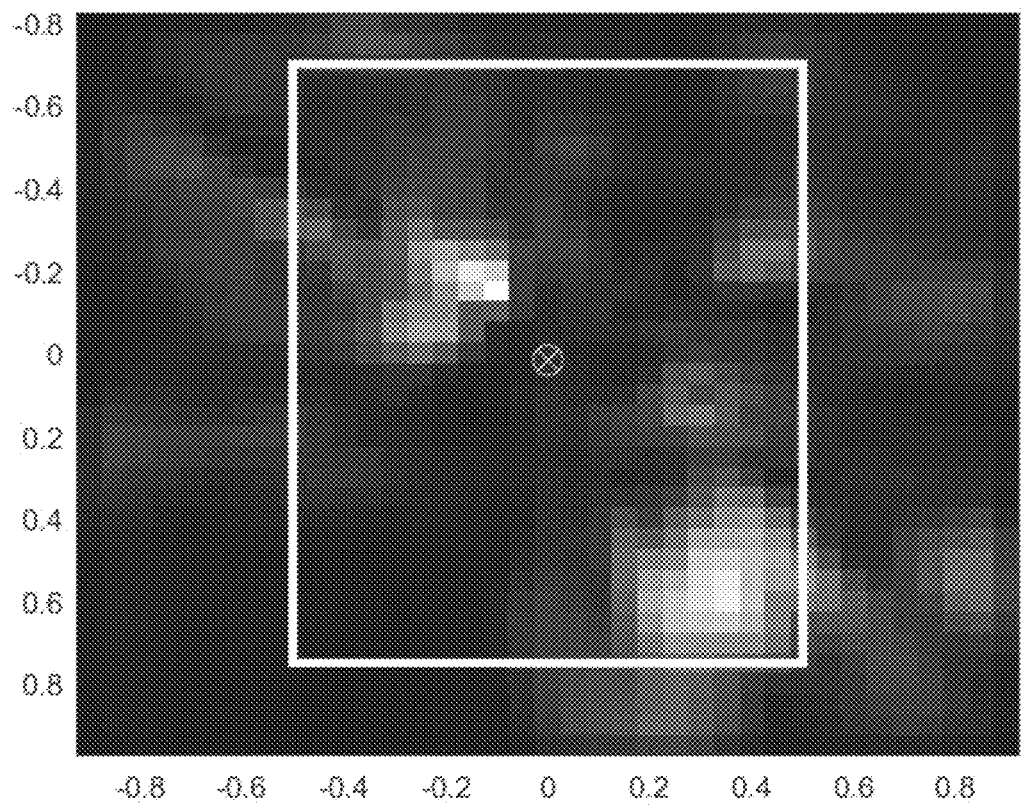
FIGS. 8a-8e depict image products at various stages of processing of passengers sitting in a car interior environment, in accordance with an embodiment of the invention.

FIG. 8a depicts a 2D top view projection of a 3D image, generated by a MIMO radar installed in the roof of the passenger cabin of the car. The image represents a single captured frame. A white rectangle has been added to indicate the boundary of the car interior. The specific scenario being shown is that of an adult sitting in the driver seat (top left corner of the white rectangle), an infant sitting in the passenger front seat (top right corner of the white rectangle), and another adult sitting in the right seat in the back row (bottom right corner of the white rectangle). As can be seen, it is extremely difficult to identify the infant, due to its low reflectivity compared to the adult passengers. Objects associated with adult passengers mask the signal reflection from the infant.

Figure 8B:
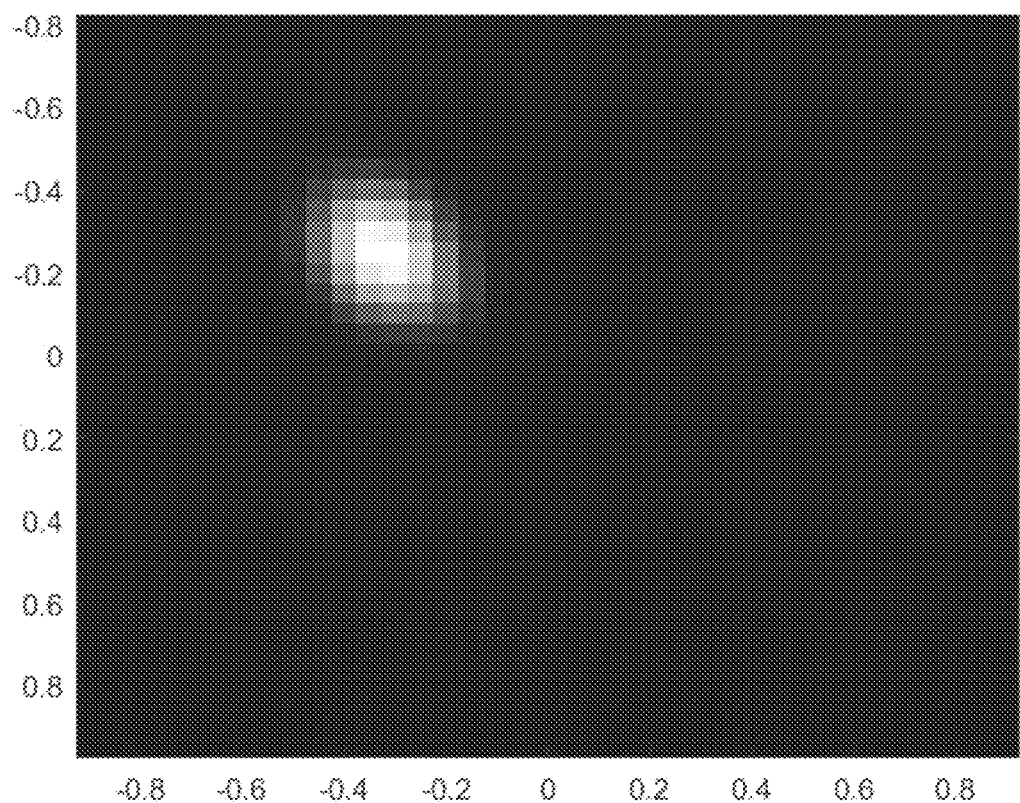
Figure 8C:
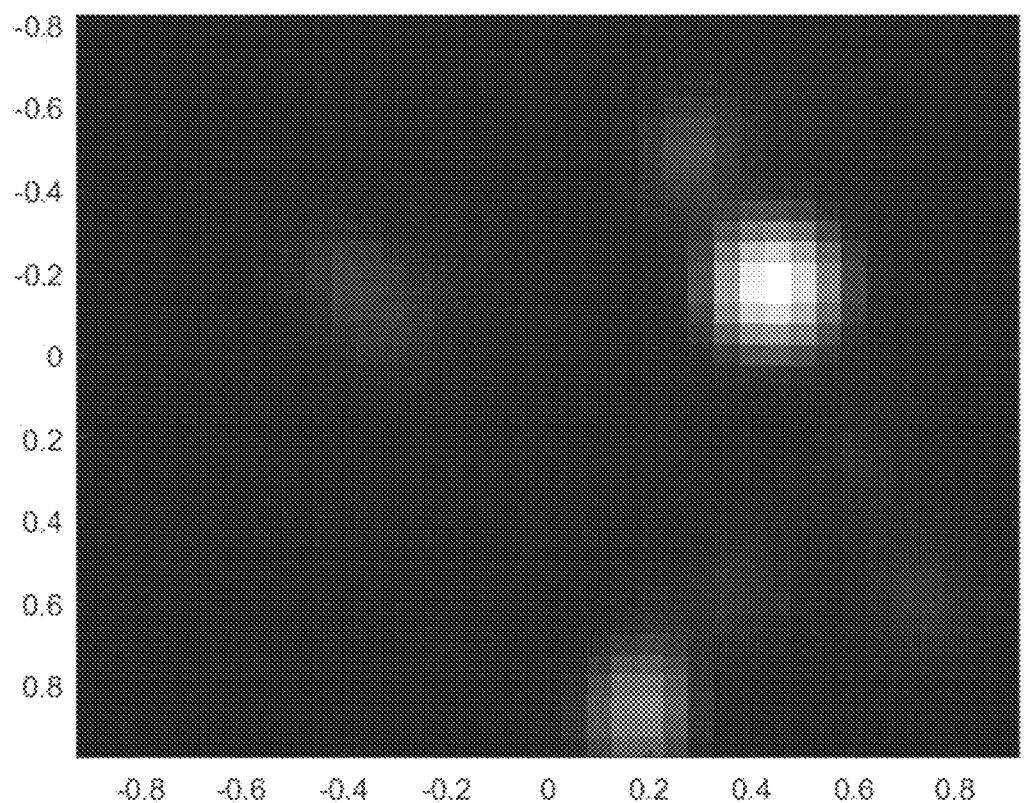
Figure 8D:
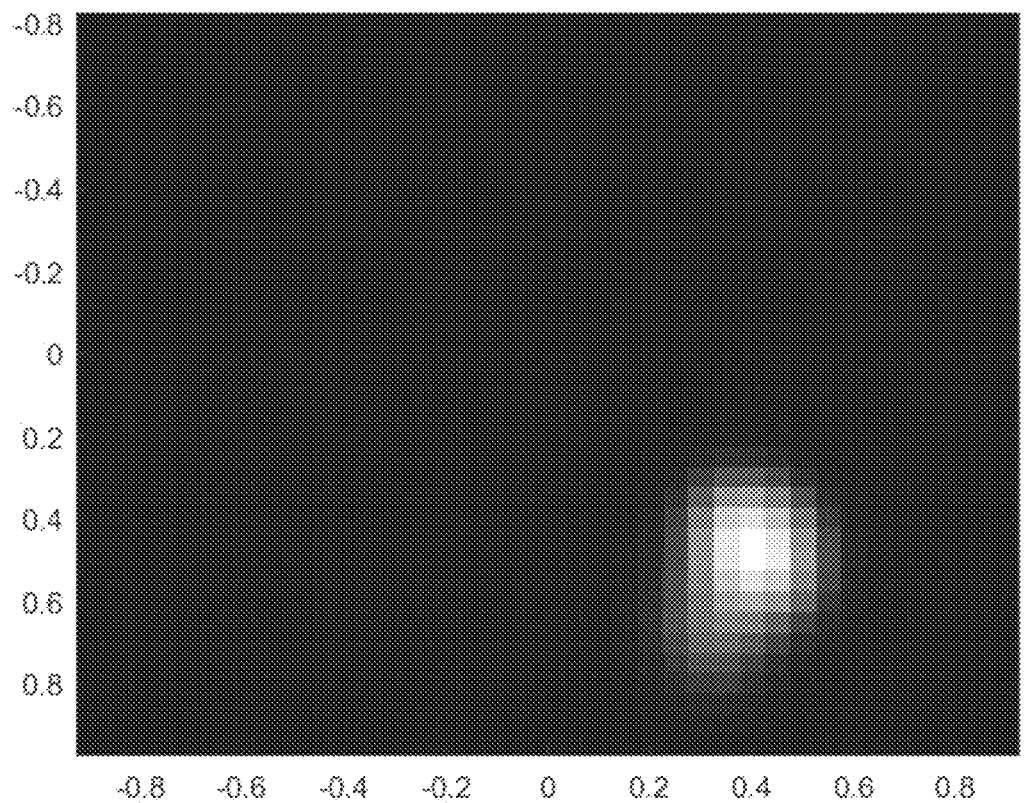

FIG. 8b, 8c, 8d, show the spatial pattern associated with thre elements which have been decomposed from a sequence of frames, by identifying the correlated motion of each individual passenger. These spatial patterns allow for an easy identification of three passengers.

Figure 8E:
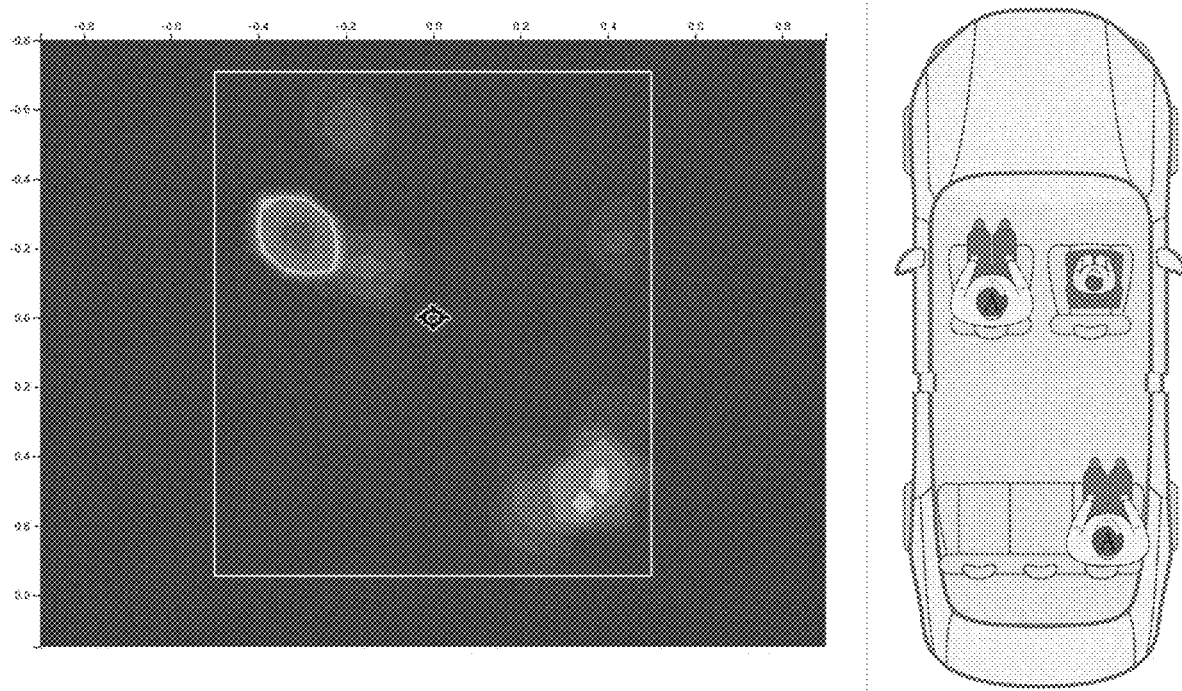

FIG. 8e shows a screenshot of a user interface, used as an output of the system. On the left side is an image produced by filtering and then recombining the spatial patterns shown in FIG. 8b, 8c, 8d. On the right side is a graphical summarization of the occupancy state reported by the system, correctly identifying the two adults and the infant in the correct positions. The classification of passengers into adults and infants is done by examining the spatial pattern for each detected element.

The separated components characterize the spatial movement modes associated with each type of movement, e.g. the spatial movement mode associated with respiration and the spatial movement mode associated with heartbeat.

The sets of voxels over which the movement is characterized can originate from a target tracking function, or it can originate form a priori knowledge, such as the candidate seating locations of persons in a car. The set of voxels may encompass multiple people, where the set of movement modes would encompass, for example, the respiration patterns of those multiple people. In the case of a moving vehicle, the spatial movement modes may include motion induced by the vibration of the vehicle, and the measured voxels may include reference objects such as empty seats. In other examples the measurement may include moving objects in the environment, such as ceiling fans, so as to separate fluctuations induced by such objects and movements induced by people of interest.

According to some embodiments, the system is be configurable to operate in various detection or activation modes; high detection mode, a medium mode, or a standby mode in which the fps and respective time durations are set by a user or manufacturer. Following are examples of activation modes:

High active mode: Capture rate of 30 frames per second (fps) for a period of 12 seconds, then a capture recess for 18 seconds, and repeating these two steps 6 sequential times (overall 3 minutes);

Medium active mode: capture rate of 10 fps for a period of 9 seconds, then a capture recess for 51 seconds, and repeating these two steps 10 sequential times (overall 10 minutes);

Standby mode: No capture for a period of 10 minutes, while former data captured and processed is saved for future analysis and comparison.

The system provides further flexibility by providing a configuration provision to activate in various activation modes, each for a predefined time or for a predetermined number of cycles or be activated by a combination of predefined time period and cycles.

Furthermore, according to some embodiments, the system can automatically change from one activation mode to another, responsively to collected data.

According to some embodiments, the system can be activated (turned "ON") manually, and according to some embodiments, the system can be automatically activated responsive to predetermined instructions (for example during specific hours) and/or a predetermined condition of another system.

Additional power saving provisions include provisions to activate a reduced number of radar, transmit/receive modules, and processors in accordance with different power consumption or activation modes.

According to some embodiments, the system can be temporarily triggered OFF or temporarily activated in a "standby" mode, for power resources conservation.

Figure 9:
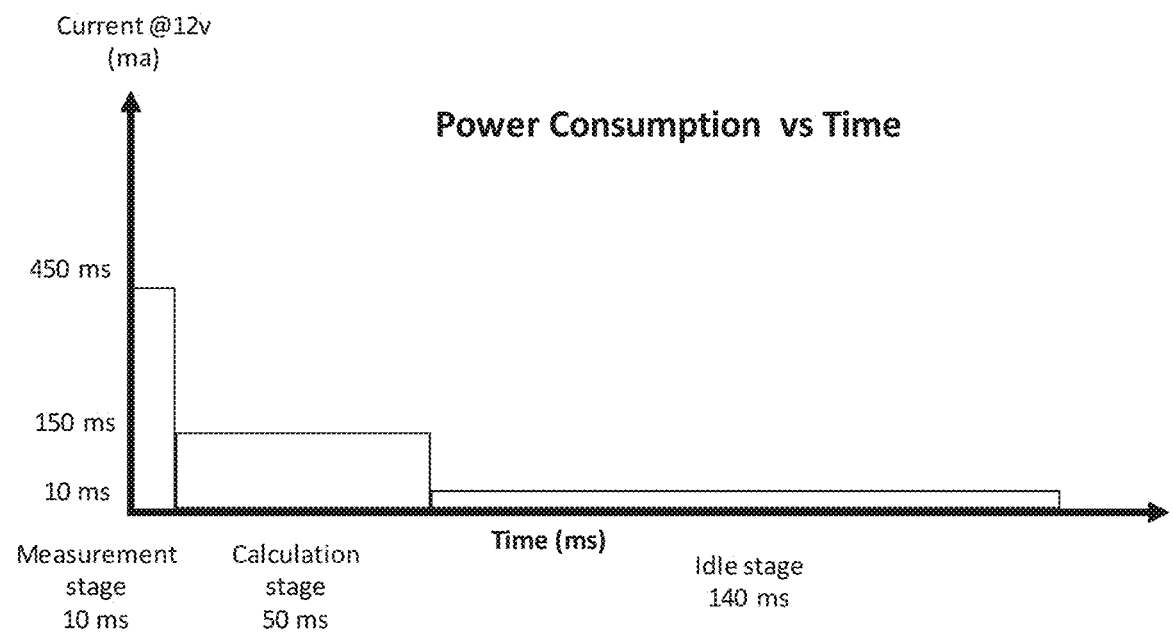
FIG. 9 is a graph depicting operating stages of one operating cycle employed during active detection modes, in accordance with an embodiment of the invention.

FIG. 9 depicts operating stages of one operating cycle employed during active detection modes, in accordance with a certain embodiment. As shown, the operating cycle includes a measurement stage, calculation stage, and an idle stage.

In the measurement stage, capture of a complex target object employs a current of 450 mA via a voltage of 12 v, for a time slot of 10 msec, at a full frame rate, for example between 15 to 25 frames per second (fps).

During the calculations stage, where calculations are executed in accordance with at least some of the above-mentioned methods to identify a motion, using a current of 150 mA via a voltage of 12 v, for a time slot of 50 msec;

During the idle stage, a current of 30 mA via a voltage of 12 v is employed, for a time slot of 140 msec to ensure memory retention previously captured or calculated data.

According to some embodiments, the methods and system mentioned above, can be implemented for various of monitoring and alerting uses. In a certain application, for example, a baby/toddler sitting in the back seat of a vehicle or in a crib is monitored. The device is configured to activate an alarm responsively to detection of a threshold variation change in breathing rate or heartbeat rate.

Another vehicular monitoring application is the field of detection of a baby or a toddler remaining in the vehicle after a threshold amount of time following engine disengagement and door locking.

In a certain embodiment the monitoring device is implemented within a vehicle to monitor occupants.

In a certain embodiment, the vehicular monitoring device is configured to be activated when the engine is OFF and/or the doors are locked in accordance with at least one of the above mentioned high and medium activation modes for a predetermined number of cycles and/or time period. The device is linked to the engine and locking system so at to provide such actuation functionality. Situations in which no motion is observed the monitoring device assumes a standby mode for a configurable time period.

According to some embodiments, the alert is selected from either activating the vehicle's horn, activating the vehicle's air ventilation, opening the vehicles windows, unlocking the vehicle, sending an alert to an application user, sending an alert to emergency services, and any combination thereof. According to some embodiments, alert is repeated until the system is manually switched OFF.

The monitoring device is configured to sequentially repeat the "monitoring" and "standby" operating modes, until: the vehicle is switched "ON", wherein the system is either manually turned OFF, automatically turned off, or continues to monitor in accordance with either the passage of a threshold period of time or a achievement of a threshold number of repetitions.

Similarly, the device can be employed to the monitor the elderly or sick at one's bed and activate an alarm responsively to a threshold variation in breathing rate, heart rate, or heart rate variability.

The device-linked alarm includes audial alarms, visual alarms, or the combination of both, and in certain embodiments the alarm is activated remotely through any of a variety of wireless technologies.

It should be appreciated that embodiments formed from combinations of features set forth in separate embodiments are also within the scope of the present invention. Furthermore, while certain features of the invention have been illustrated and described herein, modifications, substitutions, and equivalents are included within the scope of the invention.

What is claimed is:

1. A multiple-input/multiple-output radar-based system using correlated movement among parts of a complex object as a discriminatory feature to identity a complex object among a plurality of complex objects, the system comprising:

a radar antenna array;

at least one transmit/receive module configured to transmit radar signals and receive reflected radar signals through the antenna array, the system operative to:
  transmit a series of signals at set time intervals towards a plurality of complex target objects, each of the complex target objects characterized by unique, correlated movement among its parts,
  receive reflected radar signals from the complex target objects, each of the reflected radar signals having an amplitude attenuation and a phase shift relative to the transmitted radar signal in accordance with a collective correlated movement of parts of each of the complex target objects;

a configurable activation module enabling power saving measures, the activation module in communication with the transmit/receive module; and a processor coupled to the array, the processor configured to:
  render the reflected radar signals into a vector of signal values for a time frame associated with each one of the time intervals,
  stack the vectors into a signal matrix,
  decompose the signal matrix into signal elements, each of the signal elements uniquely corresponding to a correlated movement among parts of one of the complex target objects, each of the signal elements having both a spatial component and a temporal component.

2. The system of claim 1, wherein the activation module is configurable to set frame capture rate.

3. The system of claim 2, wherein the frame capture rate is defined by a threshold number of system cycles.

4. The system of claim 1, wherein the activation module is configurable to set a time slot of frame capture.

5. The system of claim 4, wherein the slot of frame capture is set in accordance with frame capture rate.

6. The system of claim 1, wherein the processor is further configured to compute a periodicity of each of the signal elements from the temporal component associated with each of the signal elements.

7. The system of claim 6, wherein the periodicity is a breathing rate or a heart rate.

8. The system of claim 1, wherein the processor is further configured to compute a variance in the heart rate.

9. The system of claim 1, wherein the unique correlated movement among parts of a complex object is selected from a group consisting of coordinated movement of body limbs, head turning, hand gesture, and changes in body posture.

10. A multiple-input/multiple-output radar-based system using correlated movement among parts of a complex object as a discriminatory feature to identity a complex object among a plurality of complex objects, the system comprising:
    a radar antenna array;
    at least one transmit/receive module configured to transmit radar signals and receive reflected radar signals through the antenna array, the system operative to:
       transmit a series of signals at set time intervals towards a plurality of complex target objects, each of the complex target objects characterized by unique, correlated movement among its parts,
       receive reflected radar signals from the complex target objects, each of the reflected radar signals having an amplitude attenuation and a phase shift relative to the transmitted radar signal in accordance with a collective correlated movement of parts of each of the complex target objects;
    a configurable activation module enabling power saving measures, the activation module in communication with the transmit/receive module; and
    a processor coupled to the array, the processor configured to:
       render the reflected radar signals into a vector of voxel values for a time frame associated with each one of the time intervals,
       stack the vectors into a voxel matrix,
       decompose the voxel matrix into voxel elements, each of the voxel elements uniquely corresponding to a correlated movement among parts of one of the complex target objects, each of the signal elements having both a spatial component and a temporal component.

11. The system of claim 10, wherein the activation module is configurable to set frame capture rate.

12. The system of claim 11, wherein the frame capture rate is defined by a threshold number of system cycles.

13. The system of claim 10, wherein the activation module is configurable to set a time slot of frame capture.

14. The system of claim 13, wherein the slot of frame capture is set in accordance with frame capture rate.

15. The system of claim 10, wherein the processor is further configured to compute a periodicity of each of the voxel elements from the temporal component associated with each of the voxel elements.

16. The system of claim 10, wherein the periodicity is a breathing rate or a heart rate.

17. The method of claim 10, wherein the processor is further configured to compute a variance in the heart rate.

18. The system of claim 10, wherein the unique correlated movement among parts of a complex object is selected from a group consisting of coordinated movement of body limbs, head turning, hand gesture, and changes in body posture.

* * * * *